(12) United States Patent
Duffy et al.

(10) Patent No.: US 10,416,088 B2
(45) Date of Patent: *Sep. 17, 2019

(54) VIRTUAL INSPECTION SYSTEMS WITH MULTIPLE MODES

(71) Applicant: KLA-Tencor Corporation, Milpitas, CA (US)

(72) Inventors: Brian Duffy, San Jose, CA (US); Saibal Banerjee, Fremont, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/784,187

(22) Filed: Oct. 16, 2017

(65) Prior Publication Data

US 2018/0052118 A1    Feb. 22, 2018

Related U.S. Application Data

(62) Division of application No. 14/803,872, filed on Jul. 20, 2015, now Pat. No. 9,816,939.

(Continued)

(51) Int. Cl.
  *G01N 21/88*  (2006.01)
  *G01N 21/95*  (2006.01)
  (Continued)

(52) U.S. Cl.
  CPC ..... *G01N 21/8851* (2013.01); *G01N 21/9501* (2013.01); *H01J 37/222* (2013.01);
  (Continued)

(58) Field of Classification Search
  USPC ......................... 382/144, 145, 149
  See application file for complete search history.

(56) References Cited

U.S. PATENT DOCUMENTS

6,539,106 B1 *  3/2003  Gallarda ............. G01R 31/307
                                                      382/149
6,621,571 B1 *  9/2003  Maeda ............... G01N 21/9501
                                                      356/237.4

(Continued)

FOREIGN PATENT DOCUMENTS

CN    103531497       1/2014
JP    2011-047724     3/2011

(Continued)

*Primary Examiner* — Ishrat I Sherali
(74) *Attorney, Agent, or Firm* — Ann Marie Mewherter

(57) ABSTRACT

Methods and systems for determining one or more characteristics for defects detected on a specimen are provided. One system includes one or more computer subsystems configured for identifying a first defect that was detected on a specimen by an inspection system with a first mode but was not detected with one or more other modes. The computer subsystem(s) are also configured for acquiring, from the storage medium, one or more images generated with the one or more other modes at a location on the specimen corresponding to the first defect. In addition, the computer subsystem(s) are configured for determining one or more characteristics of the acquired one or more images and determining one or more characteristics of the first defect based on the one or more characteristics of the acquired one or more images.

30 Claims, 9 Drawing Sheets

Related U.S. Application Data

(60) Provisional application No. 62/027,458, filed on Jul. 22, 2014.

(51) Int. Cl.
  *H01J 37/22* (2006.01)
  *H01J 37/26* (2006.01)
  *H01J 37/28* (2006.01)

(52) U.S. Cl.
  CPC .............. *H01J 37/26* (2013.01); *H01J 37/28* (2013.01); *G01N 2021/8887* (2013.01); *H01J 2237/22* (2013.01); *H01J 2237/221* (2013.01); *H01J 2237/26* (2013.01); *H01J 2237/2817* (2013.01)

(56) References Cited

U.S. PATENT DOCUMENTS

| | | | | |
|---|---|---|---|---|
| 6,759,655 | B2* | 7/2004 | Nara | G03F 7/70616 250/307 |
| 7,251,024 | B2* | 7/2007 | Maeda | G01N 21/956 250/339.11 |
| 7,310,585 | B2* | 12/2007 | Brodsky | H01L 22/20 257/E21.525 |
| 7,747,062 | B2* | 6/2010 | Chen | G01N 21/8851 382/141 |
| 8,168,950 | B2* | 5/2012 | Furuhashi | H01J 37/20 250/307 |
| 8,558,173 | B2* | 10/2013 | Nozoe | G01N 23/20 250/306 |
| 8,737,718 | B2* | 5/2014 | Sakai | G01N 21/9501 382/149 |
| 9,401,016 | B2* | 7/2016 | Kulkarni | G06T 7/74 |
| 9,601,393 | B2* | 3/2017 | Lee | G01N 21/9501 |
| 9,816,939 | B2* | 11/2017 | Duffy | G01N 21/8851 |
| 2007/0070335 | A1 | 3/2007 | Goren | |
| 2009/0297019 | A1 | 12/2009 | Zafar et al. | |
| 2010/0067780 | A1 | 3/2010 | Kawaragi | |
| 2010/0128119 | A1 | 5/2010 | Takahashi | |
| 2010/0166290 | A1 | 7/2010 | Wang et al. | |
| 2010/0246933 | A9 | 9/2010 | Hiroi et al. | |
| 2013/0128026 | A1 | 5/2013 | Hirose | |
| 2013/0294677 | A1 | 11/2013 | Urano et al. | |

FOREIGN PATENT DOCUMENTS

| | | |
|---|---|---|
| TW | 201322030 | 6/2013 |
| TW | 201423085 | 6/2014 |
| WO | 2013/109714 | 7/2013 |

\* cited by examiner

VIRTUAL INSPECTION SYSTEMS WITH MULTIPLE MODES

BACKGROUND OF THE INVENTION

1. Field of the Invention

The present invention generally relates to methods and systems for determining one or more characteristics for defects detected on a specimen.

2. Description of the Related Art

The following description and examples are not admitted to be prior art by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices. However, as the dimensions of semiconductor devices decrease, inspection becomes even more important to the successful manufacture of acceptable semiconductor devices because smaller defects can cause the devices to fail.

Many inspection tools have adjustable parameters for many of the image generation elements of the tools. In this manner, the parameters for one or more elements (such as energy source(s), polarizer(s), lens(es), detector(s), and the like) can be altered depending on the type of specimen being inspected and the characteristics of the defects of interest (DOIs) on the specimen. For example, different types of specimens may have dramatically different characteristics, which can cause the same tool with the same parameters to image the specimens in extremely different ways. In addition, since different types of DOIs can have dramatically different characteristics, inspection system parameters that are suitable for detection of one type of DOI may not be suitable for detection of another type of DOI. Furthermore, different types of specimens can have different noise sources, which can interfere with detection of DOIs on the specimens in different ways.

The development of inspection tools with adjustable parameters has also led to the increasing use of inspection processes that involve scanning the specimen with more than one combination of parameters values (otherwise referred to as "modes") such that different defect types can be detected with different modes. For example, one mode may have a greater sensitivity for detecting one type of defect while another mode may have a greater sensitivity for detecting another type of defect. Therefore, using both modes, an inspection system may be able to detect both types of defects with acceptable sensitivity.

Although using more than one mode (e.g., through a multi-channel illumination with matching multi-channel response collection) can provide advantages for defect detection, implementation has generally not been achieved in practice due to the complexity of the inspection system imaging elements and the data processing. In addition, typically in such systems, the detector output (e.g., images) that are stored for the specimen are only images produced by the mode that detected a defect (e.g., by exceeding a threshold level configured in advance by a user). In other words, when a defect is detected by one mode, the image generated for the defect by that one mode may be saved and can therefore be used post-inspection for other applications, but an image generated at the same location of the defect by another mode may not be saved if that other mode did not also detect the defect. Therefore, the image generated by the other mode that did not detect the defect may not be available for use in post-inspection defect-related functions. Furthermore, the threshold levels are separate for each mode and do not take into account the co-occurring and correlated attribute/feature values in the other modes for defect outlier detection.

Accordingly, it would be advantageous to develop systems and methods for determining one or more characteristics for defects detected on a specimen that do not have one or more of the disadvantages described above.

SUMMARY OF THE INVENTION

The following description of various embodiments is not to be construed in any way as limiting the subject matter of the appended claims.

One embodiment relates to a system configured to determine one or more characteristics for defects detected on a specimen. The system includes a storage medium configured for storing images for a specimen generated by an inspection system. The inspection system is configured for scanning energy over a physical version of the specimen while detecting energy from the specimen to thereby generate the images for the specimen and detect defects on the specimen based on the images. The inspection system is also configured to perform the scanning and the detecting with multiple modes. The images stored by the storage medium include the images generated for locations on the specimen at which the defects were and were not detected by the inspection system.

The system also includes one or more computer subsystems configured for identifying a first of the defects that was detected with a first of the multiple modes but was not detected with one or more other of the multiple modes. The computer subsystem(s) are also configured for acquiring, from the storage medium, one or more of the images generated with the one or more other of the multiple modes at a location on the specimen corresponding to the first of the defects. In addition, the computer subsystem(s) are configured for determining one or more characteristics of the acquired one or more images and determining one or more characteristics of the first of the defects based on the one or more characteristics of the acquired one or more images. The system may be further configured as described herein.

Another embodiment relates to a method for determining one or more characteristics for defects detected on a specimen. The method includes storing images for a specimen generated by an inspection system, which is configured as described above. The stored images include the images described above. The method also includes the identifying, acquiring, determining the one or more characteristics of the acquired one or more images, and determining the one or more characteristics of the first of the defects described above. The steps of the method are performed by one or more computer subsystems.

Each of the steps of the method described above may be further performed as described further herein. In addition, the embodiment of the method described above may include any other step(s) of any other method(s) described herein. Furthermore, the method described above may be performed by any of the systems described herein.

Another embodiment relates to a non-transitory computer-readable medium storing program instructions executable on a computer system for performing a computer-implemented method for determining one or more characteristics for defects detected on a specimen. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

A further embodiment relates to another system configured to detect defects on a specimen. This system includes a storage medium configured for storing images for a specimen generated by an inspections system. The inspection system is configured for scanning energy over a physical version of the specimen while detecting energy from the specimen to thereby generate the images for the specimen. The inspection system is also configured to perform the scanning and the detecting with multiple modes. The system also includes one or more computer systems configured for acquiring, from the storage medium, two or more images generated with two or more of the multiple modes at a location on the specimen and determining if a defect is present at the location based on the acquired two or more images. The system may be further configured as described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

Figure 1:
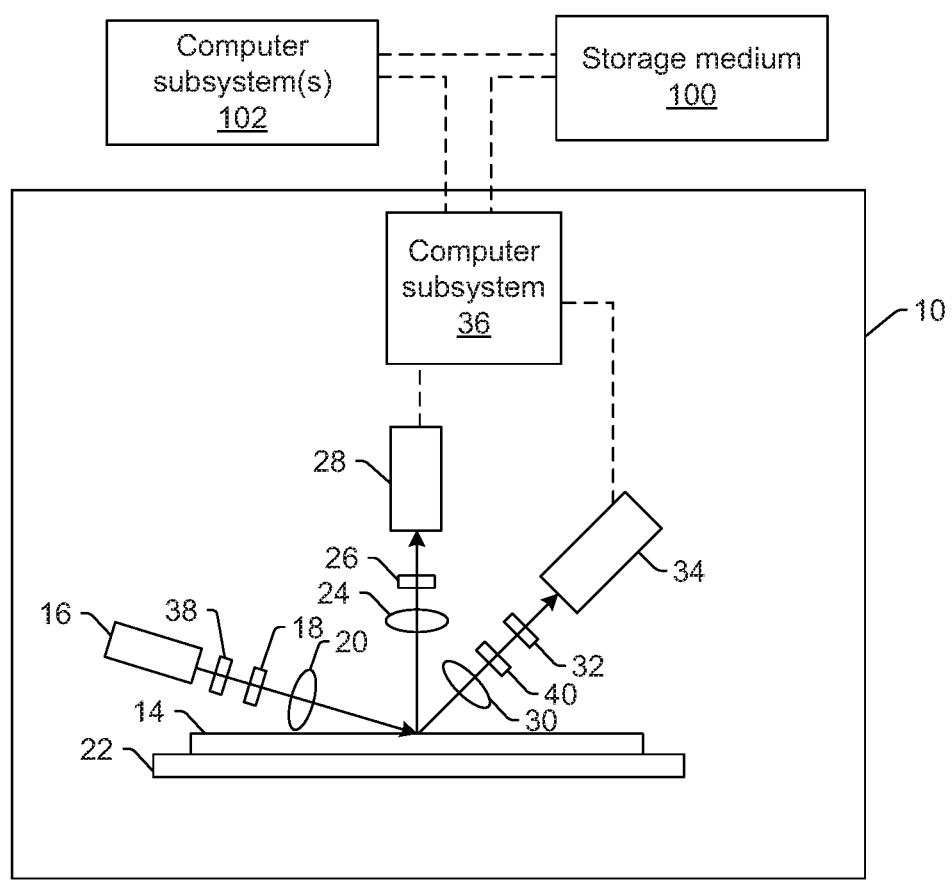
FIGS. 1 and 1*a* are schematic diagrams illustrating side views of embodiments of a system configured as described herein.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The terms "design" and "design data" as used herein generally refer to the physical design (layout) of an IC and data derived from the physical design through complex simulation or simple geometric and Boolean operations. In addition, an image of a reticle acquired by a reticle inspection system and/or derivatives thereof can be used as a "proxy" or "proxies" for the design. Such a reticle image or a derivative thereof can serve as a substitute for the design layout in any embodiments described herein that use a design. The design may include any other design data or design data proxies described in commonly owned U.S. Pat. No. 7,570,796 issued on Aug. 4, 2009 to Zafar et al. and U.S. Pat. No. 7,676,077 issued on Mar. 9, 2010 to Kulkarni et al., both of which are incorporated by reference as if fully set forth herein. In addition, the design data can be standard cell library data, integrated layout data, design data for one or more layers, derivatives of the design data, and full or partial chip design data.

In general, however, the design information or data cannot be generated by imaging a wafer with a wafer inspection system. For example, the design patterns formed on the wafer may not accurately represent the design for the wafer and the wafer inspection system may not be capable of generating images of the design patterns formed on the wafer with sufficient resolution such that the images could be used to determine information about the design for the wafer. Therefore, in general, the design information or design data cannot be generated using a physical wafer. In addition, the "design" and "design data" described herein refers to information and data that is generated by semiconductor device designers in a design process and is therefore available for use in the embodiments described herein well in advance of printing of the design on any physical wafers.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

The embodiments described herein generally relate to implementations of a virtual, multi-mode (e.g., multi-channel broadband) inspector. For example, the embodiments described herein provide the benefits of a multi-mode (e.g., multi-wavelength, multi-spectrum illumination, variable aperture, etc.) relatively high speed inspection system, with imaging capability in the image generation elements or in the electronics and substantially high precision coordinates at predetermined locations, possibly for the purpose of defect-related functions such as binning, classification, and sampling for subsequent analysis with particular focus on semiconductor wafer and reticle inspection and metrology. The embodiments described herein may be particularly helpful in differentiating locations that would otherwise be indistinguishable with other approaches. The embodiments can be implemented practically with a virtual inspector, which reduces the need for specimen passes through the inspector or other instrument.

In one embodiment, the specimen includes a wafer. In another embodiment, the specimen includes a reticle. The wafer and the reticle may include any wafer and reticle known in the art.

One embodiment relates to a system configured to determine one or more characteristics for defects detected on a specimen. One embodiment of such a system is shown in FIG. 1. The system includes storage medium 100 configured for storing images generated for a specimen by inspection system 10. The inspection system is configured for scanning energy over a physical version of the specimen while detecting energy from the specimen to thereby generate the images for the specimen and detect defects on the specimen based on the images. The inspection system is also configured to perform the scanning and the detecting with multiple modes.

In one embodiment, the energy scanned over the specimen includes light, and the energy detected from the specimen includes light. For example, in the embodiment of the system shown in FIG. 1, inspection system 10 includes an illumination subsystem configured to direct light to specimen 14. The illumination subsystem includes at least one light source. For example, as shown in FIG. 1, the illumination subsystem includes light source 16. In one embodiment, the illumination subsystem is configured to direct the light to the specimen at one or more angles of incidence, which may include one or more oblique angles and/or one or more normal angles. For example, as shown in FIG. 1, light from light source 16 is directed through optical element 18 and then lens 20 to specimen 14 at an oblique angle of incidence. The oblique angle of incidence may include any suitable oblique angle of incidence, which may vary depending on, for instance, characteristics of the specimen and the defects to be detected on the specimen.

The illumination subsystem may be configured to direct the light to the specimen at different angles of incidence at different times. For example, the inspection system may be configured to alter one or more characteristics of one or more elements of the illumination subsystem such that the light can be directed to the specimen at an angle of incidence that is different than that shown in FIG. 1. In one such example, the inspection system may be configured to move light source 16, optical element 18, and lens 20 such that the light is directed to the specimen at a different oblique angle of incidence or a normal (or near normal) angle of incidence.

In some instances, the inspection system may be configured to direct light to the specimen at more than one angle of incidence at the same time. For example, the illumination subsystem may include more than one illumination channel, one of the illumination channels may include light source 16, optical element 18, and lens 20 as shown in FIG. 1 and another of the illumination channels (not shown) may include similar elements, which may be configured differently or the same, or may include at least a light source and possibly one or more other components such as those described further herein. If such light is directed to the specimen at the same time as the other light, one or more characteristics (e.g., wavelength, polarization, etc.) of the light directed to the specimen at different angles of incidence may be different such that light resulting from illumination of the specimen at the different angles of incidence can be discriminated from each other at the detector(s).

In another instance, the illumination subsystem may include only one light source (e.g., source 16 shown in FIG. 1) and light from the light source may be separated into different optical paths (e.g., based on wavelength, polarization, etc.) by one or more optical elements (not shown) of the illumination subsystem. Light in each of the different optical paths may be then be directed to the specimen. Multiple illumination channels may be configured to direct light to the specimen at the same time or at different times (e.g., when different illumination channels are used to sequentially illuminate the specimen). In another instance, the same illumination channel may be configured to direct light to the specimen with different characteristics at different times. For example in some instances, optical element 18 may be configured as a spectral filter and the properties of the spectral filter can be changed in a variety of different ways (e.g., by changing the spectral filter) such that different wavelengths of light can be directed to the specimen at different times. The illumination subsystem may have any other suitable configuration known in the art for directing the light having different or the same characteristics to the specimen at different or the same angles of incidence sequentially or simultaneously.

In one embodiment, light source 16 may include a broadband plasma (BBP) light source. In this manner, the light generated by the light source and directed to the specimen may include broadband light. However, the light source may include any other suitable light source such as a laser. The laser may include any suitable laser known in the art and may be configured to generate light at any suitable wavelength or wavelengths known in the art. In addition, the laser may be configured to generate light that is monochromatic or nearly-monochromatic. In this manner, the laser may be a narrowband laser. The light source may also include a polychromatic light source that generates light at multiple discrete wavelengths or wavebands.

Light from optical element 18 may be focused onto specimen 14 by lens 20. Although lens 20 is shown in FIG. 1 as a single refractive optical element, it is to be understood that, in practice, lens 20 may include a number of refractive and/or reflective optical elements that in combination focus the light from the optical element to the specimen. The illumination subsystem shown in FIG. 1 and described herein may include any other suitable optical elements (not shown). Examples of such optical elements include, but are not limited to, polarizing component(s), spectral filter(s), spatial filter(s), reflective optical element(s), apodizer(s), beam splitter(s), aperture(s), and the like, which may include any such suitable optical elements known in the art. In addition, the inspection system may be configured to alter one or more of the elements of the illumination subsystem based on the type of illumination to be used for inspection.

The inspection system may also include a scanning subsystem configured to cause the light to be scanned over the specimen. For example, the inspection system may include stage 22 on which specimen 14 is disposed during inspection. The scanning subsystem may include any suitable mechanical and/or robotic assembly (that includes stage 22) that can be configured to move the specimen such that the light can be scanned over the specimen. In addition, or alternatively, the inspection system may be configured such that one or more optical elements of the inspection system perform some scanning of the light over the specimen. The light may be scanned over the specimen in any suitable fashion such as in a serpentine-like path or in a spiral path.

The inspection system further includes one or more detection channels. At least one of the one or more detection channels includes a detector configured to detect light from the specimen due to illumination of the specimen by the system and to generate output responsive to the detected light. For example, the inspection system shown in FIG. 1 includes two detection channels, one formed by collector 24, element 26, and detector 28 and another formed by collector 30, element 32, and detector 34. As shown in FIG. 1, the two detection channels are configured to collect and detect light at different angles of collection. In some instances, both detection channels are configured to detect scattered light, and the detection channels are configured to detect light that is scattered at different angles from the specimen. However, one or more of the detection channels may be configured to detect another type of light from the specimen (e.g., reflected light).

As further shown in FIG. 1, both detection channels are shown positioned in the plane of the paper and the illumination subsystem is also shown positioned in the plane of the paper. Therefore, in this embodiment, both detection channels are positioned in (e.g., centered in) the plane of incidence. However, one or more of the detection channels may be positioned out of the plane of incidence. For example, the detection channel formed by collector 30, element 32, and detector 34 may be configured to collect and detect light that is scattered out of the plane of incidence. Therefore, such a detection channel may be commonly referred to as a "side" channel, and such a side channel may be centered in a plane that is substantially perpendicular to the plane of incidence.

Although FIG. 1 shows an embodiment of the inspection system that includes two detection channels, the inspection system may include a different number of detection channels (e.g., only one detection channel or two or more detection channels). In one such instance, the detection channel formed by collector 30, element 32, and detector 34 may form one side channel as described above, and the inspection system may include an additional detection channel (not shown) formed as another side channel that is positioned on the opposite side of the plane of incidence. Therefore, the inspection system may include the detection channel that includes collector 24, element 26, and detector 28 and that is centered in the plane of incidence and configured to collect and detect light at scattering angle(s) that are at or close to normal to the specimen surface. This detection channel may therefore be commonly referred to as a "top" channel, and the inspection system may also include two or more side channels configured as described above. As such, the inspection system may include at least three channels (i.e., one top channel and two side channels), and each of the at least three channels has its own collector, each of which is configured to collect light at different scattering angles than each of the other collectors.

As described further above, each of the detection channels included in the inspection system may be configured to detect scattered light. Therefore, the inspection system shown in FIG. 1 may be configured for dark field (DF) inspection of specimens. However, the inspection system may also or alternatively include detection channel(s) that are configured for bright field (BF) inspection of specimens. In other words, the inspection system may include at least one detection channel that is configured to detect light specularly reflected from the specimen. Therefore, the inspection systems described herein may be configured for only DF, only BF, or both DF and BF inspection. Although each of the collectors are shown in FIG. 1 as single refractive optical elements, it is to be understood that each of the collectors may include one or more refractive optical element(s) and/or one or more reflective optical element(s).

The one or more detection channels may include any suitable detectors known in the art. For example, the detectors may include photo-multiplier tubes (PMTs), charge coupled devices (CCDs), and time delay integration (TDI) cameras. The detectors may also include any other suitable detectors known in the art. The detectors may also include non-imaging detectors or imaging detectors. In this manner, if the detectors are non-imaging detectors, each of the detectors may be configured to detect certain characteristics of the scattered light such as intensity but may not be configured to detect such characteristics as a function of position within the imaging plane. As such, the output that is generated by each of the detectors included in each of the detection channels of the inspection system may be signals or data, but not image signals or image data. In such instances, a computer subsystem such as computer subsystem 36 of the inspection system may be configured to generate images of the specimen from the non-imaging output of the detectors. However, in other instances, the detectors may be configured as imaging detectors that are configured to generate imaging signals or image data. Therefore, the inspection system may be configured to generate the images described herein in a number of ways.

It is noted that FIG. 1 is provided herein to generally illustrate a configuration of an inspection system that may be included in the system embodiments described herein or that may generate images that are stored and used by the system embodiments described herein. Obviously, the inspection system configuration described herein may be altered to optimize the performance of the inspection system as is normally performed when designing a commercial inspection system. In addition, the systems described herein may be implemented using an existing inspection system (e.g., by adding functionality described herein to an existing inspection system) such as the 29xx/28xx series of tools that are commercially available from KLA-Tencor, Milpitas, Calif. For some such systems, the methods described herein may be provided as optional functionality of the inspection system (e.g., in addition to other functionality of the inspection system). Alternatively, the inspection system described herein may be designed "from scratch" to provide a completely new inspection system.

Computer subsystem 36 of the inspection system may be coupled to the detectors of the inspection system in any suitable manner (e.g., via one or more transmission media, which may include "wired" and/or "wireless" transmission media) such that the computer subsystem can receive the output generated by the detectors during scanning of the specimen. Computer subsystem 36 may be configured to perform a number functions using the output of the detectors. For instance, the computer subsystem may be configured to detect defects on the specimen using the output of the detectors. Detecting the defects on the specimen may be performed by the computer subsystem by applying some defect detection algorithm and/or method to the output generated by the detectors. The defect detection algorithm and/or method may include any suitable algorithm and/or method known in the art. For example, the computer subsystem may compare the output of the detectors to a threshold. Any output having values above the threshold may be identified as a potential defect while any output having values below the threshold may not be identified as a potential defect. In another example, the computer subsystem may be configured to send the output of the detectors to a storage medium such as storage medium 100 without performing defect detection on the output. The computer subsystem of the inspection system may be further configured as described herein.

The computer subsystem of the inspection system (as well as other computer subsystems described herein) may also be referred to herein as computer system(s). Each of the computer subsystem(s) or system(s) described herein may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer subsystem(s) or system(s) may also include any suitable processor known in the art such as a parallel processor. In addition, the computer subsystem(s) or system(s) may include a computer platform with high speed processing and software, either as a standalone or a networked tool.

If the system includes more than one computer subsystem, then the different computer subsystems may be coupled to each other such that images, data, information, instructions, etc. can be sent between the computer subsystems as described further herein. For example, computer subsystem 36 of the inspection system may be coupled to computer subsystem(s) 102 as shown by the dashed line in FIG. 1 by any suitable transmission media, which may include any suitable wired and/or wireless transmission media known in the art. Two or more of such computer subsystems may also be effectively coupled by a shared computer-readable storage medium (not shown) such as storage medium 100.

Although the system is described above as being an optical or light-based inspection system, the inspection system may be an electron beam-based system. In one such embodiment, the energy source is an electron beam source, and the energy detected by the detector includes electrons. In one such embodiment shown in FIG. 1a, the inspection system includes electron column 122 coupled to computer subsystem 124.

Figure 1A:
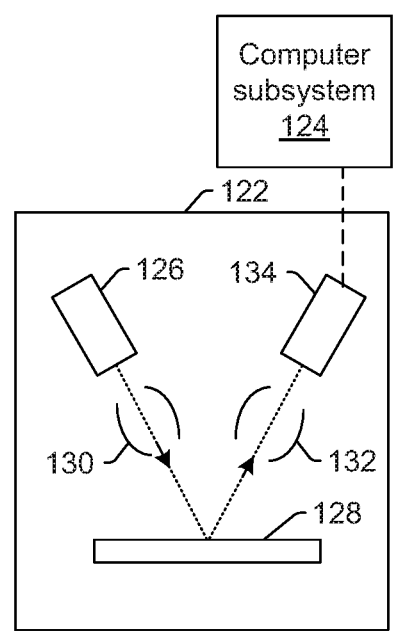

As also shown in FIG. 1a, the electron column includes electron beam source 126 configured to generate electrons that are focused to specimen 128 by one or more elements 130. The electron beam source may include, for example, a cathode source or emitter tip, and one or more elements 130 may include, for example, a gun lens, an anode, a beam limiting aperture, a gate valve, a beam current selection aperture, an objective lens, and a scanning subsystem, all of which may include any such suitable elements known in the art.

Electrons returned from the specimen (e.g., secondary electrons) may be focused by one or more elements 132 to detector 134. One or more elements 132 may include, for example, a scanning subsystem, which may be the same scanning subsystem included in element(s) 130.

The electron column may include any other suitable elements known in the art. In addition, the electron column may be further configured as described in U.S. Pat. No. 8,664,594 issued Apr. 4, 2014 to Jiang et al., U.S. Pat. No. 8,692,204 issued Apr. 8, 2014 to Kojima et al., U.S. Pat. No. 8,698,093 issued Apr. 15, 2014 to Gubbens et al., and U.S. Pat. No. 8,716,662 issued May 6, 2014 to MacDonald et al., which are incorporated by reference as if fully set forth herein.

Although the electron column is shown in FIG. 1a as being configured such that the electrons are directed to the specimen at an oblique angle of incidence and are scattered from the specimen at another oblique angle, it is to be understood that the electron beam may be directed to and scattered from the specimen at any suitable angles. In addition, the electron beam-based inspection system may be configured to use multiple modes to generate images of the specimen as described further herein (e.g., with different illumination angles, collection angles, etc.). The multiple modes of the electron beam-based inspection system may be different in any image generation parameters of the inspection system.

Computer subsystem 124 may be coupled to detector 134 as described above. The detector may detect electrons returned from the surface of the specimen thereby forming electron beam images of the specimen. The electron beam images may include any suitable electron beam images. Computer subsystem 124 may be configured to detect defects on the specimen using output generated by detector 134. Computer subsystem 124 may be configured to perform any additional step(s) described herein. A system that includes the inspection system shown in FIG. 1a may be further configured as described herein.

It is noted that FIG. 1a is provided herein to generally illustrate a configuration of an electron beam-based inspection system that may be included in the embodiments described herein. As with the optical inspection system described above, the electron beam-based inspection system configuration described herein may be altered to optimize the performance of the inspection system as is normally performed when designing a commercial inspection system. In addition, the systems described herein may be implemented using an existing inspection system (e.g., by adding functionality described herein to an existing inspection system) such as the eSxxx series of tools that are commercially available from KLA-Tencor, Milpitas, Calif. For some such systems, the methods described herein may be provided as optional functionality of the system (e.g., in addition to other functionality of the system). Alternatively, the system described herein may be designed "from scratch" to provide a completely new system.

As noted above, the inspection system is configured for scanning energy over a physical version of the specimen. In this manner, the inspection system may be configured as an "actual" inspection system, rather than a "virtual" inspection system. For example, storage medium 100 and computer subsystem(s) 102 shown in FIG. 1 may be configured as a "virtual" inspection system. In particular, the storage medium and the computer subsystem(s) are not part of inspection system 10 and do not have any capability for handling the physical version of the specimen. In other words, in inspection systems configured as virtual inspection systems, the output of its one or more "detectors" may be output that was previously generated by one or more detectors of an actual inspection system and that is stored in the virtual inspection system, and during the "scanning," the virtual inspection may replay the stored output as though the specimen is being scanned. In this manner, scanning the specimen with a virtual inspection system may appear to be the same as though a physical specimen is being scanned with an actual inspection system, while, in reality, the "scanning" involves simply replaying output for the specimen in the same manner as the specimen may be scanned. Systems and methods configured as "virtual" inspection systems are described in commonly assigned U.S. Pat. No. 8,126,255 issued on Feb. 28, 2012 to Bhaskar et al. and U.S. Patent Application Publication No. 2014/0241610 by Duffy et al. published on Aug. 28, 2014, both of which are incorporated by reference as if fully set forth herein. The embodiments described herein may be further configured as described in this patent and patent application.

As further noted above, the inspection system is configured to generate images of the specimen with multiple modes. In general, a "mode" can be defined by the values of parameters of the inspection system used for generating images of a specimen or the output used to generate images of the specimen. Therefore, modes that are different may be different in the values for at least one of the imaging parameters of the inspection system. For example, in one embodiment in which the energy scanned over the specimen and the energy detected from the specimen is light, at least one of the multiple modes uses at least one wavelength of the light scanned over the specimen that is different from at least one wavelength of the light scanned over the specimen used for at least one other of the multiple modes. The modes may be different in the wavelength scanned over the specimen as described further herein (e.g., by using different light sources, different spectral filters, etc.) for different modes. In another embodiment, at least one of the multiple modes uses an illumination channel of the inspection system that is different from an illumination channel of the inspection system used for at least one other of the multiple modes. For example, as noted above, the inspection system may include more than one illumination channel. As such, different illumination channels may be used for different modes.

In an additional embodiment, at least one of the multiple modes uses a configuration of an aperture of the inspection system that is different from a configuration of an aperture of the inspection system used for at least one other of the multiple modes. The aperture may be an illumination aperture (i.e., an aperture positioned in the path of the energy directed to the specimen) such as aperture 38 shown in FIG. 1 or a collection aperture (i.e., an aperture positioned in the path of the energy collected from the specimen) such as aperture 40 shown in FIG. 1. For example, if energy is directed to the specimen in different paths for different modes, then different apertures having at least one different characteristic (e.g., shape or size) may be positioned in the different paths. In another example, if energy is directed to the specimen in the same path for different modes, then different apertures having at least one different characteristic may be positioned in the path at different times to sequentially generate images for the specimen. In similar manners, the aperture in the path of energy from the specimen may be different for different modes by having different apertures having at least one different characteristic in the path of different energy from the specimen or by switching the aperture in the path of the energy between different scans with different modes.

As described above, therefore, the different modes may be different in illumination and/or collection/detection. The different modes may also or alternatively have other differences in collection/detection. For example, in one embodiment, at least one of the multiple modes uses a detection channel of the inspection system that is different from a detection channel of the inspection system used for at least one other of the multiple modes. In some such embodiments, as described further above, the inspection system may include multiple detection channels. Therefore, one of the detection channels may be used for one mode and another of the detection channels may be used for another mode. Furthermore, the modes may be different from each other in more than one way described herein (e.g., different modes may have one or more different illumination parameters and one or more different detection parameters).

The images stored by the storage medium include the images generated for locations on the specimen at which the defects were and were not detected by the inspection system. In other words, unlike many inspection systems and methods that store only images for locations on the specimen at which defects or potential defects have been detected, the embodiments described herein preferably store all of the images that are generated for a specimen during inspection regardless of whether or not defects were detected in the images. In this manner, in some embodiments, the images stored by the storage medium include all of the images generated for the specimen by the inspection system during the scanning and detecting. In other words, the embodiments described herein may use stored full specimen images generated with any modes.

In addition, unlike some methods and systems (such as those used for setup of an inspection recipe) in which images for one or more (but no more than a few) discrete locations on a specimen (typically locations corresponding to defects of interest (DOIs)) are generated with multiple modes and then evaluated collectively to determine which mode is most suitable for inspection of the specimen, the images that are stored by the embodiments described herein and used to perform various functions are images that have been generated by scanning a relatively large area on the specimen (i.e., as would be performed in a regular specimen inspection process after inspection recipe setup). In other words, the images stored by the storage medium preferably are images that are generated as the energy is scanned over a relatively large area on the specimen (e.g., an area on the specimen that is substantially larger than a single defect on the specimen and includes areas on the specimen that may and may not include defects). As such, the area on the specimen for which the images are generated and stored is an area having unknown defectivity. Furthermore, the scanning and inspecting described herein that generates the images that are stored are not performed for the purposes of inspection recipe or process setup. In addition, the scanning and inspecting described herein that generate the images that are stored are not performed at locations of known defects on the specimen, but are performed to determine if there are any defects present on the specimen.

In some embodiments, the images generated for the location on the specimen, at which the defects were and were not detected by the inspection system, and stored by the storage medium are generated by the inspection system in the same inspection performed by the inspection system on the specimen. For example, as described further herein, different modes may be used simultaneously or serially to generate images for a specimen during an inspection process. Therefore, different scenarios for extracting images or output for a defect or a specimen can be used and may vary depending on whether the image processing performed for defect detection is performed by processing the image planes in parallel or serially. The choice in approach may have numerous implications on the software, algorithms, and even hardware that are used for a practical implementation. For example, parallel image processing may include recording all (or all but one if a live inspection is synched for one of the modes) n "image modes" or "image planes" as described herein (e.g., in a virtual inspection system). In addition, the virtual inspector may be configured to enable streaming parallel image channels to a processor (e.g., image computer). In such configurations, storing the images as described herein may be performed using three-dimensional image data matrices, rather than two-dimensional image data matrices, in which two of the dimensions are the traditional x and y and the third dimension is the data for each of the imaging conditions. For each image pixel in the x,y plane, therefore, there would be a set of n values (one from each imaging channel).

In this manner, even though some of the embodiments described herein may use images that are generated with multiple modes of a system, the images do not necessarily have to be generated in different inspection processes performed for the specimen. As such, after an inspection process has been performed for the specimen and the images generated during that inspection process have been stored to the storage medium as described herein, all of the images that the computer subsystem(s) use to perform one or more of the functions described herein can likely be retrieved from the storage medium, which should eliminate any need to move the specimen back into the inspection system for additional image generation. For example, as described further herein, the computer subsystem(s) may perform several functions for a defect that has been detected on a specimen during an inspection process. Therefore, by storing all of the images or other output that is generated during an inspection process without regard to whether defects were or were not detected in the images or other output means that after the inspection process, the computer subsystems can, for any defect detected using at least one mode, access the images for the defects generated by other modes. As such, unlike other systems and methods that may be currently available, the embodiments described herein do not need to collect point-by-point images or other data for each location on the specimen that has been determined to be of interest by reloading the specimen onto the inspector and repeating data collection with full rescans or point-by-point imaging. Either way, this would be substantially expensive (e.g., 5-10× more expensive than a virtual inspector depending on the virtual inspector configuration) relative to achieving this with persistent images of the initial inspection area for each mode that was initially run.

In another embodiment, the inspection system is configured to perform the scanning and the detecting with the multiple modes serially in different scans of the specimen performed during a single inspection process for the specimen. In an additional embodiment, the inspection system is configured to perform the scanning and the detecting with at least two of the multiple modes simultaneously in a single scan of the specimen performed during a single inspection process for the specimen. Therefore, a single inspection process can include one or more scans of a specimen that can be performed serially and/or simultaneously with two or more modes. For example, if different modes are defined by different detection channels, then if the detection channels can detect light from the specimen simultaneously during a scan, then images can be generated simultaneously for the specimen with the different modes. However, if different modes are defined by different parameters of the same detection channel, the parameters of the detection channel can be changed between scans that are performed serially. In either case, if multiple modes are used serially or simultaneously to generate images for a specimen in a single inspection process, which are stored as described herein, then all of the images that are used to perform one or more functions described herein can be retrieved by the computer subsystem(s) from the storage medium and without performing additional scanning of the specimen after the single inspection process.

Figure 2:
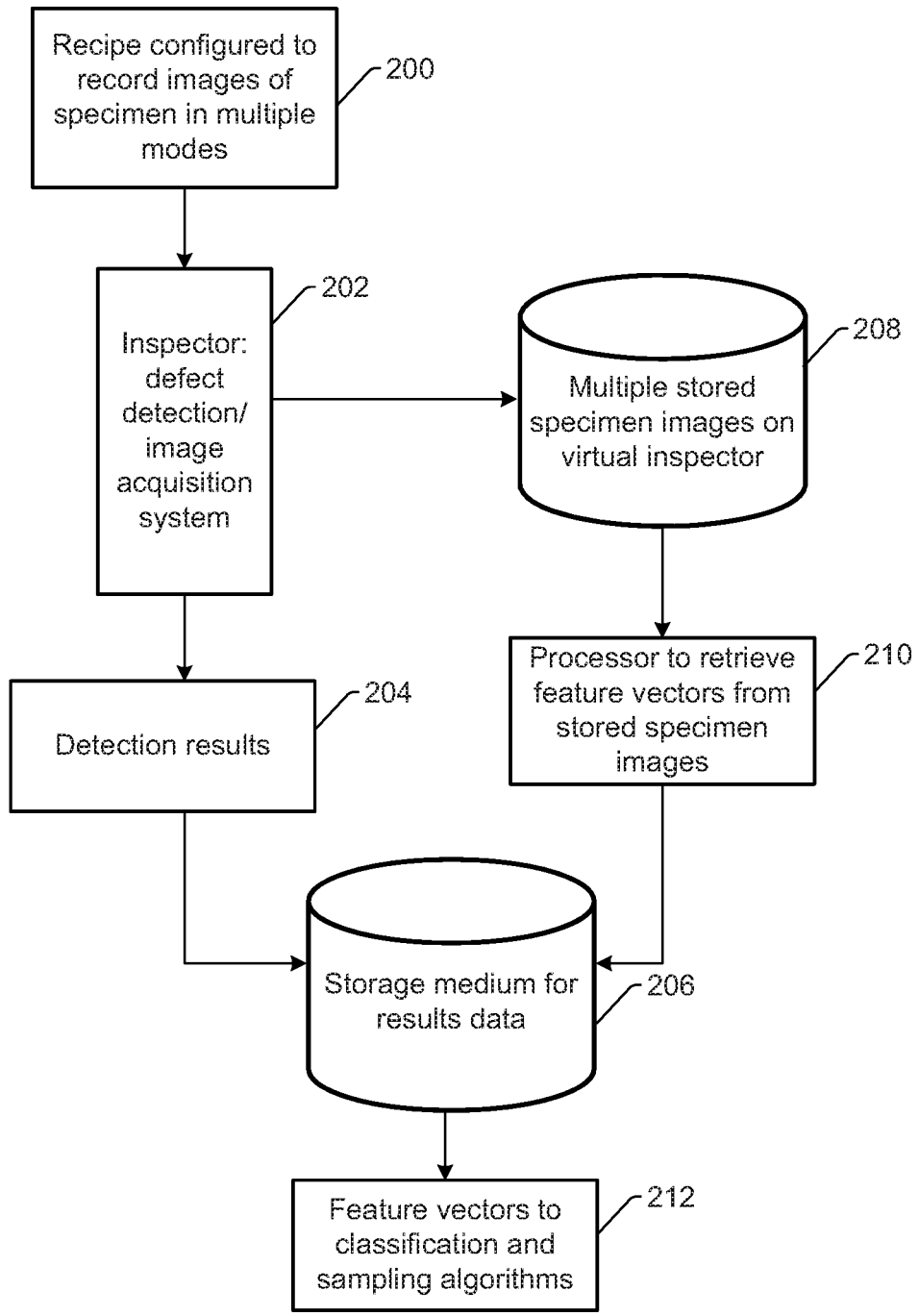
FIGS. 2-4 and 7 are flow charts illustrating different embodiments of functions that the systems described herein may be configured to perform.

In some embodiments, the systems described herein may be configured as shown in FIG. 2 in which inspector 202, which may include a defect detection and/or image acquisition system configured as described further herein, performs recipe 200 that is configured to record images of a specimen in multiple modes. The inspection recipe may generate images of the specimen in the multiple modes as described further herein. The inspector may generate detection results 204 if the inspector is configured to perform defect detection based on the images. The detection results may be sent to storage medium 206 for results data. In some instances, storage medium may be a storage medium different than the one that stores the images generated by the inspector. In other words, storage medium 206 may be different than the storage medium of the virtual inspectors described herein. Storage medium 206 may also have any other suitable configuration known in the art such as one of those described herein and may be configured as, for example, a fab database.

As further shown in FIG. 2, the images generated by the inspector during performance of the recipe may be sent to storage medium 208. In this manner, the storage medium may have stored therein multiple stored specimen images generated in multiple modes. This storage medium may part of a virtual inspection system or may be coupled to a virtual inspection system. Storage medium 208 may be further configured as described herein.

The one or more computer subsystems are configured for identifying a first of the defects that was detected with a first of the multiple modes but was not detected with one or more other of the multiple modes. The computer subsystem(s) may be configured to identify such a defect by comparing defect detection results corresponding to the different modes at the same locations on the specimen. For example, the computer subsystem(s) may compare first defect detection results generated at one location on the specimen with a first mode to second defect detection results generated at the one location on the specimen with a second mode. If the first defect detection results indicate that a defect was detected at the one location but the second defect detection results do not indicate that a defect was detected at the one location (or vice versa), then the defect may be identified as the first defect.

Although embodiments are described herein with respect to a first of the defects, it is to be understood that the computer subsystem(s) may be configured to perform the functions described herein for more than one defect. The embodiments will be described with respect to a single defect to simplify the description of the embodiments to thereby promote better understanding of the embodiments. Obviously, the computer subsystem(s) may be configured to perform one or more of the functions described herein for any, all, or only some of the defects detected on the specimen. Furthermore, the defects that are identified and for which the computer subsystem(s) perform one or more functions may include defects that are detected in any manner described herein.

The computer subsystem(s) are also configured for acquiring, from the storage medium, one or more of the images generated with the one or more other of the multiple modes at a location on the specimen corresponding to the first of the defects. For example, as shown in FIG. 2 in step 210, a processor may retrieve feature vectors from the stored specimen images. The processor may be a processor of the virtual inspection system. However, the processor may be a different processor that is not part of the virtual inspection system but is coupled to the virtual inspection system.

It would, therefore, be advantageous to be able to identify images generated by multiple modes at the same location on the specimen by leveraging the coordinate accuracy of the inspection system, which allows retrieval of the multi-mode response data at substantially precise locations of interest (e.g., locations that met the detection criteria in any of the image acquisition modes) for conditions in which there was no defect detected. For example, the embodiments described herein are preferably configured for extremely precise relocation of regions or points of interest at the deep sub-pixel level (e.g., single pixel relocation accuracy) of virtual inspector image retrieval with corrections for pixilation error (e.g., interpolation).

In some embodiments, determining which of the images correspond to the same defect or location on the specimen may be performed by aligning multiple images to a common reference such as a design. Aligning the images to each other may be further performed as described in U.S. Pat. No. 7,676,077 to Kulkarni et al. issued on Mar. 9, 2010, U.S. Pat. No. 8,041,103 to Kulkarni et al. issued on Oct. 18, 2011, and U.S. Pat. No. 8,139,843 to Kulkarni et al. issued on Dec. 17, 2013, which are incorporated by reference as if fully set forth herein. The embodiments described herein may be further configured to perform any step(s) described in these patents and may be further configured as described in these patents.

Additional examples of methods and systems that may be used to determine images generated with different modes (e.g., different focus offsets) corresponding to the same location on the specimen are described in commonly assigned U.S. Patent Application Ser. No. 62/105,979 filed by Chen et al. on Jan. 21, 2015, which is incorporated by reference as if fully set forth herein. The embodiments described herein may be further configured to perform any step(s) described in these patents and may be further configured as described in these patents.

In this manner, improvement in the coordinate accuracy for stored virtual inspection images, which enables the level of localization desired for advanced processes, may be achieved by extending the technologies used currently for registering images to design coordinates. In addition, the ability to precisely identify image data generated with different modes at the same specimen location may be aided by configuring the imaging and data handling of the system such that the input images (or the images generated by the detectors) meet substantially high coordinate precision (ideally identical pixel size and position in each image).

Figure 3:
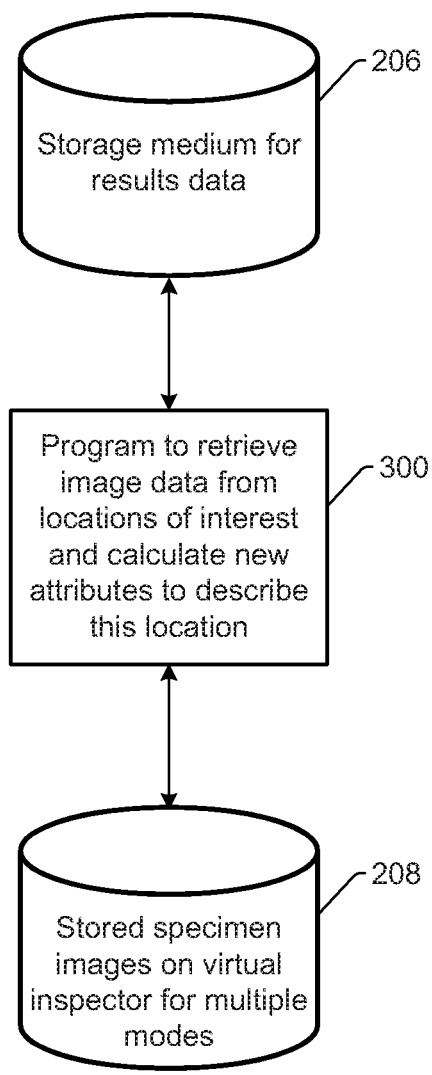

The computer subsystem(s) are further configured for determining one or more characteristics of the acquired one or more images. For example, as shown in FIG. 3, the embodiments described herein may be configured to include program 300 that retrieves image data from locations of interest on the specimen and calculates new attributes to describe this location. The image data that is retrieved by program 300 may be retrieved from storage medium 208, which may be configured as described further herein, that includes stored specimen images on a virtual inspector for multiple modes. The locations of interest may be determined based on information retrieved from storage medium 206 for results data described further herein.

In one embodiment, at least one of the acquired one or more images includes a test image, and determining the one or more characteristics of the at least one of the acquired one or more images includes generating a difference image by subtracting a reference image for the at least one of the acquired one or more images from the test image and determining one or more characteristics of the difference image. Such difference image attributes in different modes, for selected locations that did not meet some criteria for being identified as a defect or potential defect location in at least one of the different modes, may be used as described further herein for the purpose of improved differentiation in the physical nature of the locations.

In some embodiments, the first of the defects was detected in two different difference images generated for the location on the specimen corresponding to the first of the defects. In other words, the defect may include a defect detected by double arbitration type defect detection, in which a defect is detected in both comparisons performed by the double arbitration type defect detection.

In another embodiment, the first of the defects was detected in only one of multiple difference images generated for the location on the specimen corresponding to the first of the defects. In this manner, the defect may include a defect detected by single arbitration type defect detection, in which a defect is detected by a single comparison performed for defect detection, or in only one of two comparisons performed for double arbitration type defect detection, and so would not necessarily be identified as a defect by defect detection.

Figure 5:
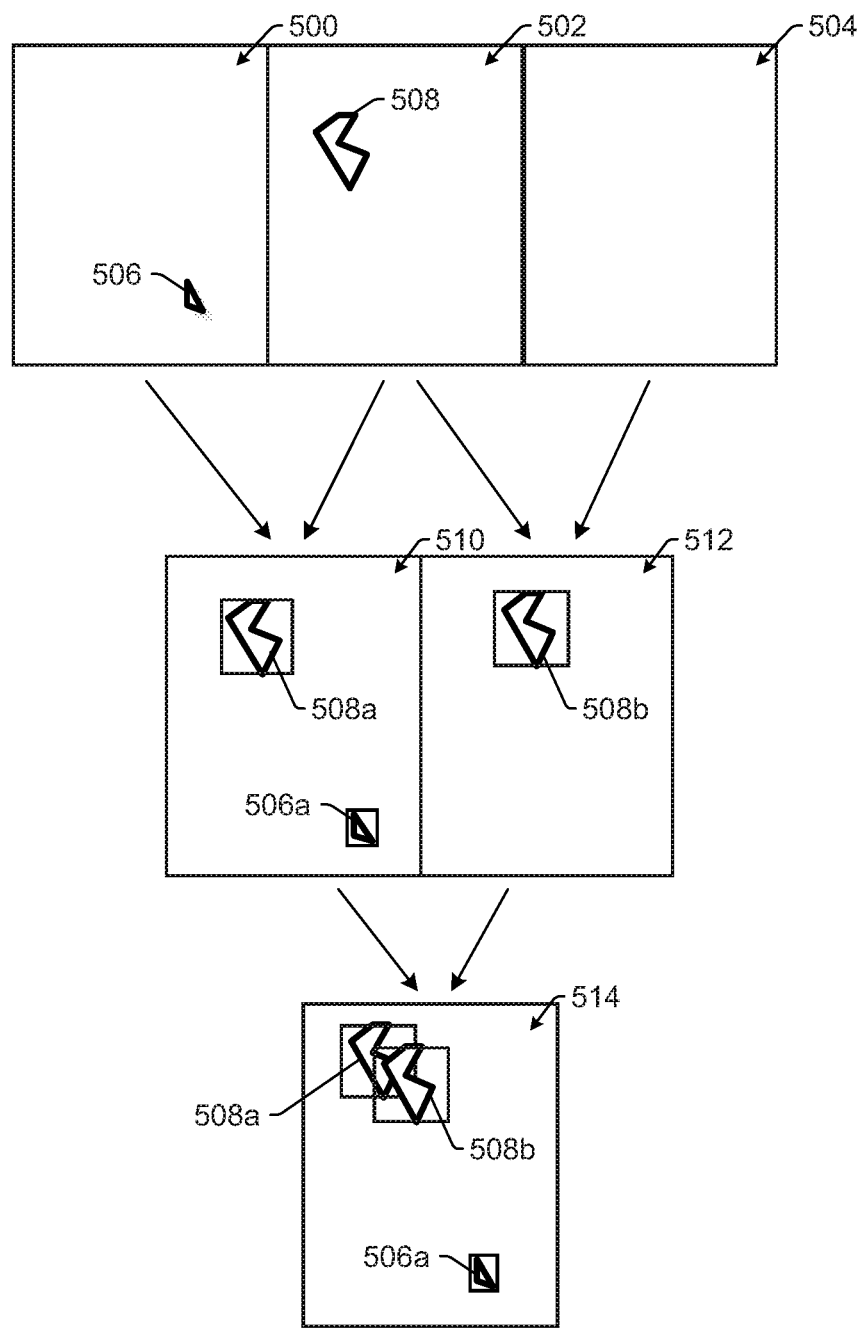
FIG. 5 is a schematic diagram illustrating a plan view of one example of different defects that can be detected by the system embodiments described herein.

In this manner, the results of defect detection algorithms and/or methods can be used to determine the "defects" or locations on the specimen for which the computer subsystem(s) perform one or more functions. In this manner, the defect detection algorithms and/or methods may effectively select the locations for which the other functions described herein are performed. In one such example, as shown in FIG. 5, in three dies 500, 502, and 504 on a specimen, there may be two defects 506 and 508. The three dies may be located side-by-side on the specimen and therefore may be scanned one after the other on the specimen. As such, defect detection may be performed using the output of the inspection system generated by scanning the three dies. For example, the output generated for dies 500 and 502 may be compared to each other, and the output generated for dies 502 and 504 may be compared to each other. The comparisons may involve subtracting the output for one of the dies from the other of the dies to thereby generate difference images. For example, subtracting the output for die 500 from the output for die 502 may produce difference image 510 while subtracting the output for die 504 from the output of die 502 may produce difference image 512. Such difference image generation may be performed when die 502 is considered the "test die" and dies 500 and 504 are considered the "reference dies" for that test die. Therefore, such difference image generation may be performed for double arbitration type defect detection for die 502.

Defect detection may then be performed using the difference images, e.g., by applying a threshold to the difference images although more complex types of defect detection may be performed on the difference images. As further shown in FIG. 5, when defect detection is performed on difference image 510, portions 506a and 508a of the difference image corresponding to defects 506 and 508 may be identified as defects. In contrast, when defect detection is performed on difference image 512, portion 508b of the difference image corresponding to defect 508 may be identified as a defect. However, in a double arbitration type scheme, the difference image detection results may be compared to identify the defects that were in detected in only one difference image and the defects that were detected in both difference images. For example, results 514 of such a comparison would show that defective image portions 508a and 508b were detected in both difference images and defect 508 was therefore "doubly caught" while defective image portion 506a was detected in only one of the difference images and defect 506 therefore was "singly caught." As such, in a double arbitration type scheme, defect 508 may be reported by the defect detection algorithm and/or method while defect 506 would not. However, defect 506 may be an actual defect even though it is only singly caught by the defect detection described above.

Double arbitration type defect detection schemes may therefore be modified such that information (e.g., specimen location) for events that are detected only singly may be stored, and the embodiments described herein may be configured to select such events as the first of the defects for additional consideration described herein. In this manner, as described further herein, events that are singly caught and are actual defects can be separated from events that are singly caught but are not actual defects. However, the defects that are identified for additional consideration described herein may also include doubly caught defects. For example, even if a defect is detected in two comparisons of a double arbitration type detection scheme, that defect may be detected by fewer than all of the modes used for inspection. Therefore, using information generated for the location of that defect on the specimen by other modes, which did not produce output that resulted in defect detection, additional attributes of the defect may be determined that may be useful for other functions performed for the defect such as classification, sampling, review, etc.

Figure 6:
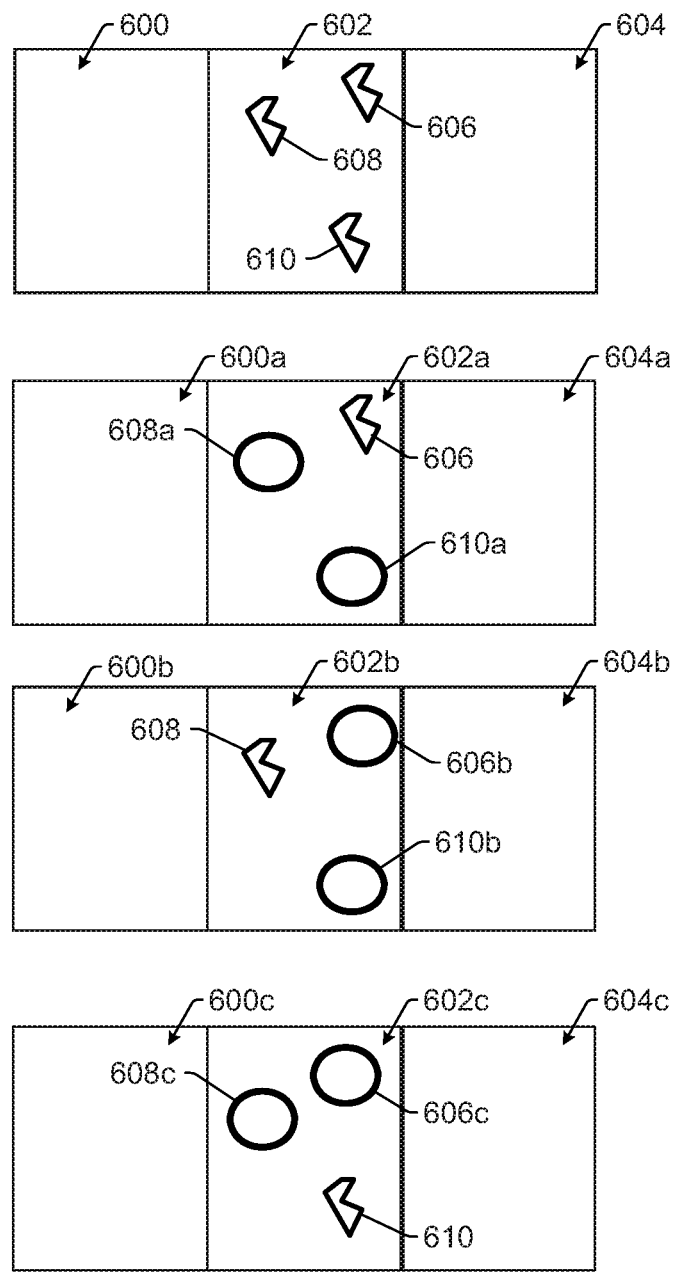
FIG. 6 is a schematic diagram illustrating a plan view of one example of defects and different portions of images in which the defects were not detected that can be used to determine characteristics of the defects according to the embodiments described herein.

In one such example shown in FIG. 6, three dies 600, 602, and 604 on a specimen (not shown in FIG. 6) may be scanned by an inspection system during an inspection process with multiple modes. Die 602 may include three defects 606, 608, and 610. Images 600a, 602a, and 604a may be generated for dies 600, 602, and 604, respectively, with mode a, images 600b, 602b, and 604b may be generated for dies 600, 602, and 604, respectively, with mode b, and images 600c, 602c, and 604c may be generated for dies 600, 602, and 604, respectively, with mode c.

In a double arbitration type detection scheme in which dies 600 and 604 are used as reference dies for die 602, in mode a, the comparisons detected only defect 606, in mode b, the comparisons detected only defect 608 while in mode c, the comparisons detected only defect 610. Therefore, all of defects 606, 608, and 610 are detected by at least one mode but not all of the modes. In other words, each of defects 606, 608, and 610 were detected by one mode but were not detected by one or more other modes. Therefore, each or any of the defects shown in FIG. 6 may be selected as a first defect for which one or more other functions described herein are performed. As such, as described further herein, attributes of defects detected in at least one mode may be extracted from un-selected, or non-defective, locations of images generated in other modes.

For instance, if defect 606 is selected as the "first of the defects," since this defect was not detected by mode b or mode c, the images acquired at the location of this defect by these modes may be acquired from a storage medium as described herein. In particular, in this instance, portion 606b in die image 602b generated by mode b may be acquired at the location in the die image corresponding to the location of defect 606 and portion 606c in die image 602c generated by mode c may be acquired at the location in die image 602c corresponding to the location of defect 606. One or more characteristics of these portions of the images may then be determined (individually or collectively) and then these characteristics can be used as described further herein.

In a similar manner, if defect 608 is selected as the "first of the defects," since this defect was not detected by mode a or mode c, the images acquired at the location of this defect by these modes may be acquired from a storage medium as described herein. In particular, in this instance, portion 608a in die image 602a generated by mode a may be acquired at the location in the die image corresponding to the location of defect 608, and portion 608c in die image 602c may be acquired at the location in die image 602c corresponding to the location of defect 608. One or more characteristics of these portions of the images may then be determined (individually or collectively) and then these characteristics can be used as described further herein.

In addition, if defect 610 is selected as the "first of the defects," since this defect was not detected by mode a or mode b, the images acquired at the location of this defect by these modes may be acquired from a storage medium as described herein. In particular, in this instance, portion 610a in die image 602a generated by mode a may be acquired at the location in the die image corresponding to the location of defect 610 and portion 610b in die image 602b generated by mode b may be acquired at the location in die image 602b corresponding to the location of defect 610. One or more characteristics of these portions of the images may then be determined (individually or collectively) and then these characteristics can be used as described further herein.

The one or more characteristics of the acquired one or more images may include any of the image characteristics described herein such as gray level intensity. The one or more characteristics of the acquired one or more images may also be determined from the acquired images themselves or from other images generated from the acquired images. For example, the acquired images may be used to generate difference images as described further herein and then the characteristic(s) of the difference images may be determined by the computer subsystem(s). Other types of images such as median images, mean images, average images, etc. may be used in a similar manner.

The computer subsystem(s) are also configured for determining one or more characteristics of the first of the defects based on the one or more characteristics of the acquired one or more images. For example, the information for the one or more characteristics of the acquired one or more images adds defect attributes that enable the separation of defect (location) types that may not be discernable with conventional means. In other words, the embodiments described herein provide the capability to separate defects that are physically different but are indistinguishable with currently used systems and methods.

In this manner, the specimen images that are stored to the virtual inspector in multiple modes preferably cover a broad spectrum in order to gather differentiating signals from defect types that have physically different constructs (e.g., materials, locations in the process stack, location within the device structures, etc.). For example, it is known from optical simulation and empirical evidence that the detection (measurement) of specific differences between physical structures (e.g., structure disruption or variants in an intact structure) through image-to-image or image-to-reference comparisons achieve different results for different illumination and energy collection configurations. The embodiments described herein leverage the converse perspective in which the separation of locations that have different responses can be used to infer that the locations have different physical characteristics (e.g., different material composition, shape, size, etc.). By using separate recordings sent to a virtual inspector (e.g., serially), the essence of a system that stimulates and detects multi-mode responses (e.g., multi-band responses) across entire specimens can be achieved. The tradeoff may be the time to make the serial recordings. The benefit is that the result is equivalent to that which could only be achieved with a genuine multi-mode (e.g., multi-channel, multi-spectrum, etc.) system that is not likely to be implemented for practical and economic reasons. For example, an alternative to the embodiments described herein is to build an extremely complex inspector that can generate and collect the required signals simultaneously.

In this manner, in some embodiments, an inspection process may be completed for a specimen for each of the recorded modes (which can happen during recording). A relatively high accuracy relocation of the area or point of interest (e.g., on test and reference images) and analysis with attribute generation algorithms and/or methods may be performed. Data collected in this manner may also be merged with data collected through conventional detection methods. For example, as shown in FIG. 2, the defect feature vectors that are retrieved by a processor from the stored images in step 210 may be sent to storage medium 206 that also includes the detection results 204. In addition, rather than simply storing the different information in the same storage medium, the different information can be combined into one results file as described further herein such that the file includes all of the information generated for any one defect on a defect-by-defect basis. The resulting array of values for each location may constitute a full matrix of conventionally collected and unconventionally collected data across the selected mode space.

The one or more characteristics of the first of the defects determined based on the one or more characteristics of the acquired image(s) may include any suitable defect attributes or features that can be determined from images generated by inspection. In addition, the one or more characteristics of the first defect may be determined based on a combination of two or more of the characteristics of the acquired one or more images. For example, the one or more characteristics of the first of the defects may be determined as a function of two or more characteristics of the acquired image(s). Alternatively, different characteristics of the first defect may be determined individually based on characteristics of different acquired image(s). Those separately determined defect characteristics may then be combined to determine additional characteristics or information for the defect. For example, the one or more characteristics of the defect may be determined as a function of the two or more characteristics determined for the defect in images generated by different modes.

In another embodiment, the computer subsystem(s) are configured for acquiring, from the storage medium, two or more images generated with two or more of the multiple modes at an additional location on the specimen and determining if a defect is present at the additional location based on the acquired two or more images. For example, the embodiments described herein can be configured to perform one or more functions such as defect detection for any one location on the specimen using all of the images for that location generated with all of the modes used for inspection regardless of whether or not a defect was detected at that location. In particular, by virtue of the full stored images across multiple modes, the embodiments described herein provide the unique ability to efficiently get the "spectral response" in all modes used for scanning of a specimen even for undetected defects on the specimen. In addition, such embodiments leverage the persistence of "full" specimen images at any mode in combination with coordinate accuracy which allows retrieval of data at any specimen location in any mode. The specimen images that are recorded and stored to a virtual inspector in multiple modes preferably cover a relatively broad spectrum in order to differentiate defect signals from background.

As such, the embodiments described herein can be configured for full co-occurring attribute/feature-based, holistic defect detection performed on a multi-mode virtual inspector (e.g., a virtual multi-channel broadband inspector). In other words, the embodiments described herein provide the benefits of a multi-mode (e.g., multi-channel illumination) inspection system for the detection of defects and harvest the unique opportunity that a multi-mode system (e.g., multi-band illumination, variable aperture, etc.) high speed imaging system provides to detect defects (i.e., outliers) in higher dimensional spaces by considering the full co-occurring set of attributes/features holistically at every location on a semiconductor wafer or reticle. As will be described further herein, the embodiments provide the additional and holistic consideration of the full set of co-occurring image attributes/features at every location on a specimen in different modes for the purpose of improved defect detection sensitivity using multi-dimensional outlier detection methods. The embodiments described herein are particularly helpful in identifying defect locations that would otherwise be buried in background noise with conventional approaches. In addition, example purposes for developing the inspection described herein on a semiconductor wafer or reticle include review/classification or metrology.

Since the images described herein can be stored for every location on a specimen that is scanned regardless of whether or not a defect has been detected at the locations, defect detection may not be performed by the actual inspection system during or after scanning of the specimen by the actual inspection system. In other words, defect detection during image recording is not a requirement of the embodiments described herein. In this manner, the embodiments described herein may be configured for pure specimen image recording on a virtual inspector without the necessity of inspection.

Figure 4:
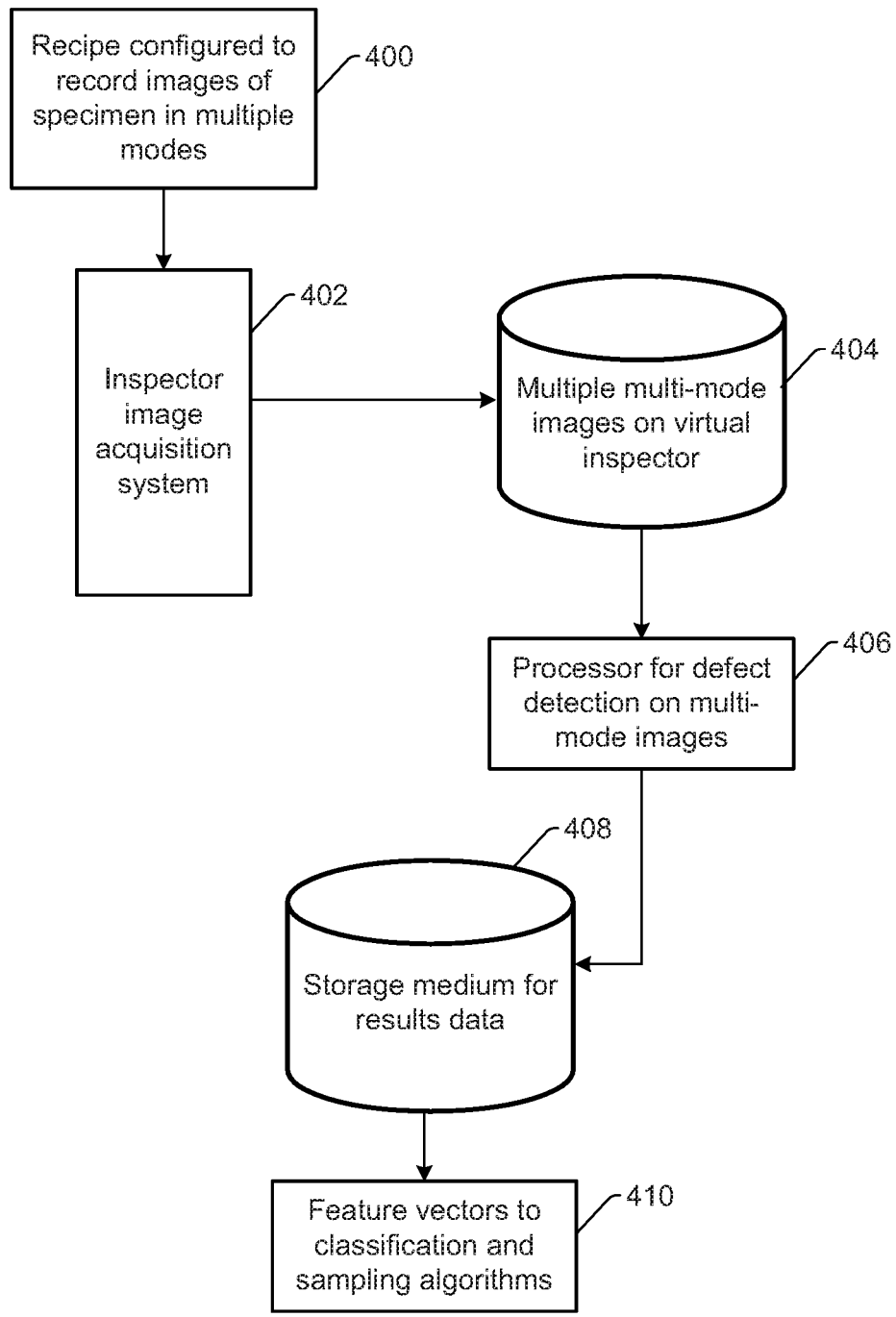

For example, as shown in FIG. 4, recipe 400 configured to record images of a specimen in multiple modes may be performed by inspector image acquisition system 402. The recipe and the image acquisition system may be further configured as described herein. The images generated by the image acquisition system (which may include any of the images described herein, e.g., serially acquired images) may be stored as described herein in storage medium 404. The storage medium may, therefore, include multiple multi-mode images on a virtual inspector.

The virtual inspector may be configured for multi-mode playback in which different images generated in different modes are played back simultaneously for any one location on the specimen. In this manner, all of the images generated with at least two modes of the inspection system can be input to data processing simultaneously such that they can be processed together. Therefore, the input to processor 406 may be vector input for mode 1, mode 2, mode 3, . . . mode n. As such, like other embodiments described herein, an important aspect of making the embodiments described herein practical is an improvement in the ability to achieve single pixel relocation accuracy in each mode on virtual inspector image retrieval.

The processor may then perform defect detection on the multi-mode images. The results of the defect detection performed by the processor (scalar detection results) may then be stored to storage medium 408 for the results data. As described further herein, the detection results data may then be sent as feature vectors 410 to classification and sampling algorithms. The defect detection that can be performed as shown in FIG. 4 can provide improvements in outlier (defect) detection as described further herein. For example, performing defect detection based on multi-mode images played back from a virtual inspector can leverage the correlation between these configurations to tease out defects that may not be detectable in any one single configuration.

Figure 8:
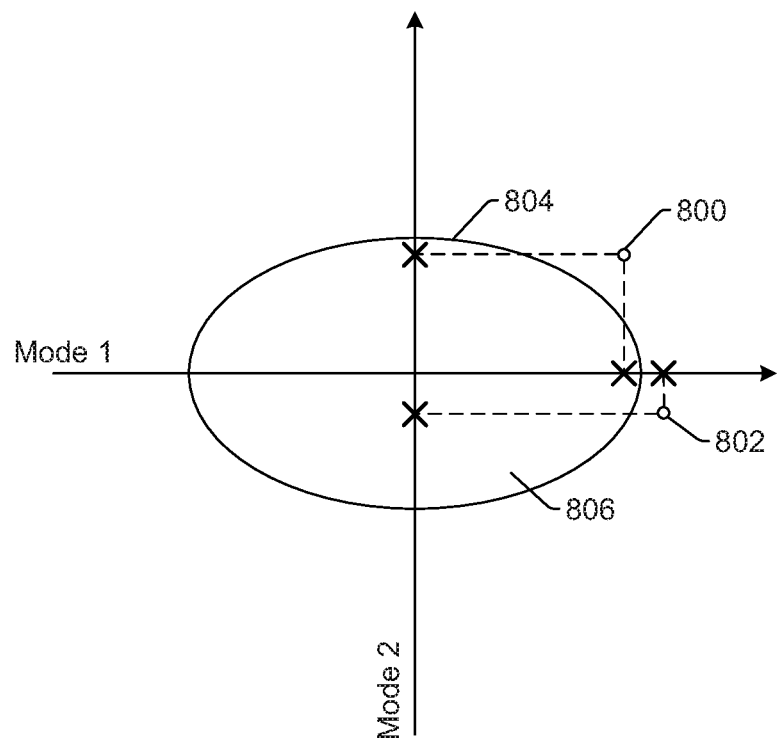
FIG. 8 is a plot illustrating one example of different defect features and how the different defect features can be used for defect detection that can be performed according to the embodiments described herein.

In one such embodiment, determining if the defect is present includes determining two or more difference images for the acquired two or more images, respectively, determining two or more difference image attributes for the two or more difference images, respectively, and determining if a defect is present based on a combination of the two or more difference image attributes. For example, FIG. 8 is a scatter plot of difference gray levels of mode 1 and mode 2 on different axes of the plot and the points in the plot correspond to different locations on the specimen. In this example, two pixel locations 800 and 802 are shown in the plot based on their difference gray levels in the different modes. Assume that a specimen location would be determined to be a defect location if and only if its difference gray levels are outside of boundary 804, which may be referred to as a "defect decision boundary," of ellipse 806. Then, it is clear from FIG. 8 that locations 800 and 802 would be identified as defect locations.

However, if one considered each difference gray level separately, i.e., without the simultaneous consideration of both gray levels, then locations 800 and 802 might not be considered to be defect locations at all. Considering each difference gray level separately may be equivalent to considering only the feet of the projections of the difference gray levels shown by the dashed lines in FIG. 8. In this case, one might not be able to extract defective pixel 800 because the points corresponding to the feet in these projections marked by X's on the x and y axes are well within the defect decision boundary of the ellipse. In addition, one might also not be able to extract defective pixel 802 because although one of its points corresponding to one of its feet marked by an X on the x axis is outside of the defect decision boundary of the ellipse, the other X is inside of the defect decision boundary of the ellipse. Therefore, location 802 may be considered defective if mode 1 was used for defect detection but not defective if only mode 2 was used for defect detection.

In an additional embodiment, determining if the defect is present includes determining two or more image attributes for the acquired two or more images, respectively, and determining if a defect is present based on a combination of the two or more image attributes. Determining if defects are present in this embodiment may be performed in the same manner as other embodiments described herein. For instance, the difference image attributes used in the defect detection described above may be replaced with attributes of any other suitable images.

In some embodiments, determining if the defect is present includes determining two or more image attributes for the acquired two or more images, respectively, and applying a multi-dimensional threshold to a combination of the two or more image attributes. For example, the virtual inspection system recording process may be completed for each of the imaging conditions. This recording process may be performed during an inspection; however, this is not a necessity. A substantially high accuracy co-localization in every mode of each specimen location with attribute/feature extraction may be performed. The resulting vector of image attribute/feature values at each location may be used to perform holistic defect detection using a multi-dimensional outlier detection algorithm.

Figure 7:
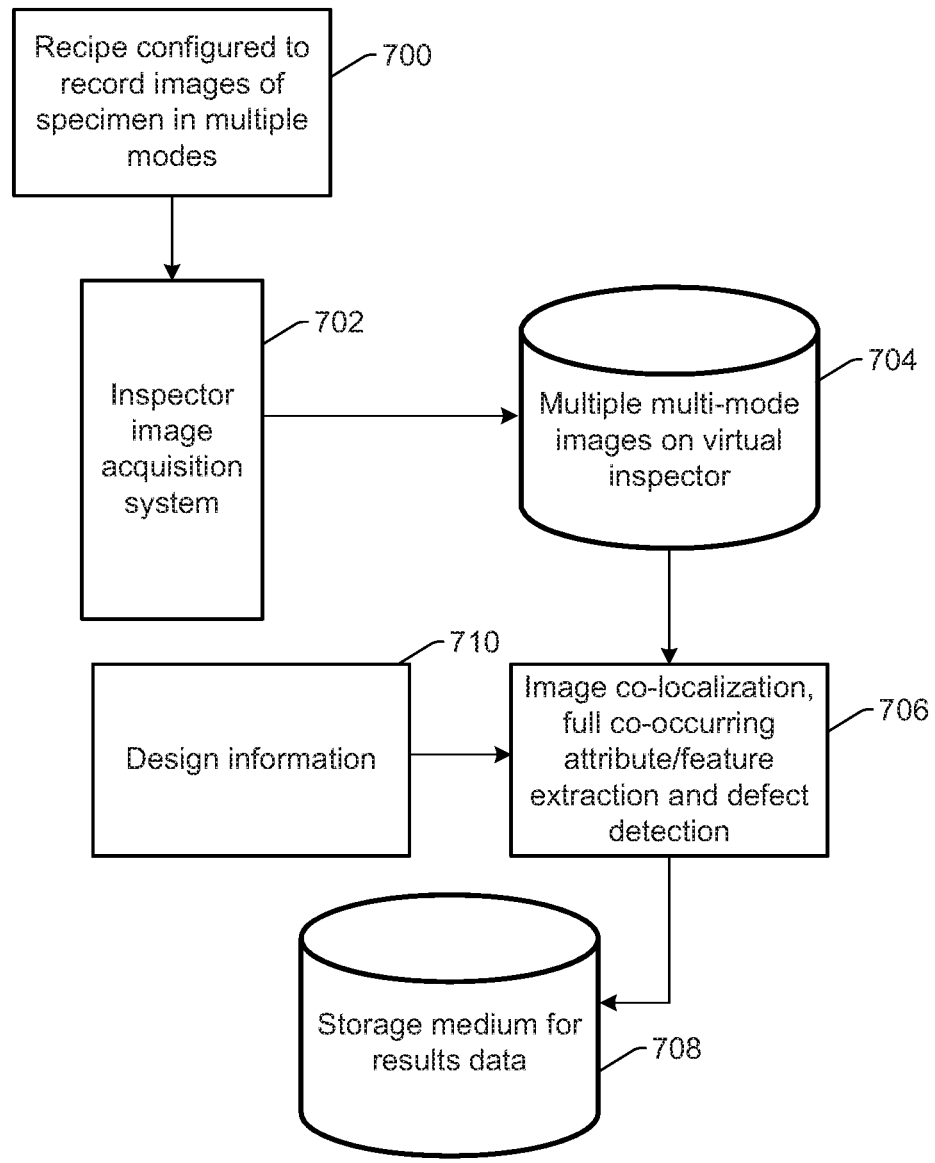

In one such example shown in FIG. 7, recipe 700 configured to record images of a specimen in multiple modes may be used by inspector image acquisition system 702. The recipe and the inspection system may be further configured as described herein. The images generated by the inspector using the recipe may then include multiple multi-mode images on a virtual inspector that may be stored in storage medium 704 as described further herein. The storage medium may be configured as described further herein. Based on the images stored in the virtual inspector, the computer subsystem(s) described herein may be configured for image co-localization, full co-occurring attribute/feature extraction and defect detection as shown in step 706. The computer subsystem(s) may then store results of this step in storage medium 708 for results data, which may be performed as described further herein. This storage medium may also be configured as described further herein.

A preferred embodiment for this defect (i.e., outlier) detection using a d-dimensional vector f of image attribute/feature values at location (x,y) on the specimen is described as follows. Associate a d-dimensional ellipsoid at coordinate location (x,y) of the specimen with: a) a d×d positive definite matrix S describing its shape (correlations), normalized by volume, e.g., by setting determinant S to unity; b) an origin of the ellipsoid at the d-dimensional vector μ (mean); and c) a threshold scalar value t that specifies the boundary (i.e., decision hyper-surface) of the ellipsoid used for outlier identification. Then, the coordinate location (x,y) is considered to have a defect if and only if $$(f-\mu)'S^{-1}(f-\mu) \geq t.$$

The learning of the parameters S, μ, and t can be performed during a training/setup phase and can be conditioned on local design or segment information as described further herein. Also, this idea can be generalized to any closed decision hyper-surface for added flexibility in choosing parameters (with increases in model complexity).

Although some embodiments are described herein with respect to a multi-dimensional threshold that has an ellipsoidal shape and two-dimensions, the embodiments described herein are not limited to such shapes and such dimensions. For example, the shape defined by the defect decision boundary can be any other shape and the number of dimensions may be any suitable number, which may be equal to the number of modes being considered by the computer subsystem(s). In fact, given the arbitrary nature of the surface generated by the embodiments described herein, the embodiments may generate and use a union of decision hyper-surfaces for detecting defects. Furthermore, although some embodiments are described herein as using a multi-dimensional threshold for defect detection, the embodiments may use a combination of two or more image attributes determined from two or more images generated with two or more modes, respectively, in a variety of other ways for defect detection. For example, the defect detection may be performed using a Boolean expression of attributes (e.g., thresholded gray scale values) from multiple modes and gray scale differences between reference and test images that express the rule for being an outlier event. One can even train a statistical classifier for this sort of defect detection, instead of it being rule-based.

In a further embodiment, the one or more computer subsystems are configured for determining one or more parameters used for determining if the defect is present based on a portion of a design for the specimen corresponding to the additional location. For example, the defect detection parameters can be conditioned upon design shapes. In addition, the stored images can be conditioned on the local design information thereby adding unprecedented defect detection capabilities that enable the separation of defect from background and that may not be achievable with conventional means. In one such example, as shown in FIG. 7, design information 710 (from a source such as a design database server) may be acquired by the computer subsystem(s) that perform image co-localization, full co-occurring attribute/feature extraction and defect detection as shown in step 706. In this manner, the computer subsystem(s) may perform these steps based on the design information.

In an additional embodiment, the one or more computer subsystems are configured for determining one or more parameters used for determining if the defect is present based on a segment of the acquired two or more images in which the additional location is located. For example, the defect detection parameters can be conditioned upon image segments. In addition, the stored images can be conditioned on image segment information thereby adding unprecedented defect detection capabilities that enable the separation of defect from background and that may not be achievable with conventional means. Different segments in the images may be determined based on the images themselves (e.g., based on properties of the images such as noise) as described in U.S. Pat. No. 8,611,639 to Kulkarni et al. issued on Dec. 17, 2013, which is incorporated by reference as if fully set forth herein. The embodiments described herein may be configured to perform any step(s) of any method(s) described in this patent and may be further configured as described in this patent.

Detecting defects using specimen images generated with multiple modes and stored in a storage medium is not limited to the embodiments described herein. For example, detecting defects on a specimen using images generated with multiple modes and stored in a storage medium such as a virtual inspector may also or alternatively be performed as described in U.S. Pat. No. 7,554,656 issued on Jun. 30, 2009 to Shortt et al., U.S. Pat. No. 7,711,177 issued on May 4, 2010 to Leslie et al., U.S. Pat. No. 7,796,804 issued on Sep. 14, 2010 to Bhaskar et al., U.S. Pat. No. 8,831,334 issued on Sep. 9, 2014 to Luo et al., U.S. Pat. No. 8,912,495 issued on Dec. 16, 2014 to Lange, and U.S. Pat. No. 9,053,527 issued on Jun. 9, 2015 to Lang et al., U.S. Patent Application Publication Nos. 2014/0219544 by Wu et al. published on Aug. 7, 2014, 2014/0270474 by Huang et al. published on Sep. 18, 2014, 2014/0285657 by Hwang et al. published on Sep. 25, 2014, 2014/035983 by Kolchin et al. published on Dec. 4, 2014, and 2015/0043804 by Huang et al. published on Feb. 12, 2015, and U.S. patent application Ser. No. 14/612,192 filed on Feb. 2, 2015 by Guo et al. (published as U.S. Patent Application Publication No. 2015/0221076 on Aug. 6, 2015), Ser. No. 14/674,856 filed on Mar. 31, 2015 by Chen et al. (now U.S. Pat. No. 9,766,186 issued on Sep. 19, 2017), and Ser. No. 14/707,592 filed on May 8, 2015 by Kulkarni et al. (now U.S. Pat. No. 9,401,016 issued on Jul. 26, 2016), all of which are incorporated by reference as if fully set forth herein. The embodiments described herein may be configured to perform any step(s) of any method(s) described in these patents, patent application publications, and patent applications and may be further configured as described in these patents, patent application publications, and patent applications.

Detecting defects only after image acquisition for the specimen has been completed and the images have been stored in the virtual inspector may be the most practical implementation for detecting defects when simultaneously considering images generated with multiple modes. For example, an inspection tool that can simultaneously generate the multi-mode images described herein and perform defect detection during such image generation may be extremely complex and possibly expensive to build. However, performing the defect detection described herein during image generation is certainly not impossible. On the other hand, it may be physically impossible to generate images with some modes simultaneously (depending on the configuration of the inspection system and which modes are to be used for defect detection). In such instances, no defect detection may be performed until after all of the images for all of the image modes that are to be used for defect detection have been generated and stored.

In this manner, another embodiment relates to a system configured to detect defects on a specimen. This system includes a storage medium configured for storing images for a specimen generated by an inspection system. The storage medium may be configured as described herein and as shown in FIG. 1. The inspection system is configured for scanning energy over a physical version of the specimen while detecting energy from the specimen to thereby generate the images for the specimen. The inspection system is also configured to perform the scanning and the detecting with multiple modes. The inspection system may be configured as described herein and as shown in FIGS. 1 and 1a.

In this embodiment, however, the inspection system is not configured to perform defect detection for the specimen. In this manner, defects are not detected on the wafer by the inspection system. Instead, one or more computer subsystems are configured for acquiring, from the storage medium, two or more images generated with two or more of the multiple modes at a location on the specimen and determining if a defect is present at the location based on the acquired two or more images.

The computer subsystem(s) may be further configured as described herein and shown in FIG. 1. The computer subsystems(s) may be configured to perform the acquiring and determining if a defect is present according to any of the embodiments described herein. The computer subsystem(s) may be further configured as described herein and may be configured to perform any other functions described herein.

In some embodiments, the computer subsystem(s) are configured for binning, classifying, or sampling the first of the defects based on the determined one or more characteristics of the first of the defects. For example, as shown in FIG. 2, feature vectors 212 in storage medium 206 may be sent to classification and sampling algorithms. Therefore, the information for the defects that is used for classification, sampling, and other functions may include information that is generated by standard defect detection that is performed by an inspection system as the inspection system scans a specimen as well as other information that is determined based on the stored images retrieved from a virtual inspection system. The defects that are classified by the computer subsystem(s) in this manner may include defects that are detected by the actual inspection system (e.g., during scanning) and/or defects that are detected based on the images stored in the virtual inspection system. The binning, classifying, and sampling may be performed in any suitable manner.

The one or more characteristics of a defect determined based on two or more images acquired with different modes are particularly valuable input data for a SEM review/classification sampling algorithm or metrology tool sample selection. In particular, in semiconductor wafer and reticle processing, SEM review/classification and metrology processes typically suffer from under-sampling so the more data from relatively high coverage data that can be used to differentiate unique defect events, the more effective the sampling can be at helping discover new defect types or extraordinary metrology sites.

The sampling of the defects that is performed based on the characteristic(s) determined as described herein may include any suitable type of sampling such as diversity sampling described is U.S. Pat. No. 9,037,280 issued on May 19, 2015 to Dishner et al., which is incorporated by reference as if fully set forth herein, and which may include selecting a sample of defects having the greatest diversity in a characteristic such that the most different (or most diverse) defects can be selected. Selecting the defects having the most different values of any one characteristic can result in a defect sample that includes unique types of defects thereby enabling better defect discovery. In addition, the embodiments described herein can be integrated into a defect discovery system or method that optimizes with full automation of data acquisition from a virtual inspector and inclusion in sampling schemes for defect SEM review/ classification and metrology.

The embodiments described herein have a number of advantages and can be used for multiple modes that are different in any manner known in the art. The embodiments also may be particularly advantageous for modes that are different in certain ways. For example, the interaction between electromagnetic radiation and matter is a well understood phenomenon, and analysis/inspection instruments are currently available that are based on the principles of spectral imaging. However, for relatively high data rate and relatively high volume applications such as semiconductor wafer and reticle inspection, it is not technically or economically practical to make direct use of spectral imaging while meeting traditional requirements of substantially high area coverage, substantially high spatial resolution, along with substantially high spectral resolution. The benefits of spectral imaging may, however, be at least partially realized by approximating the spectral response with multiple passes of the imaging system using different imaging conditions for each pass (e.g., spectrum, aperture, focus offset, etc.).

To process the multi-mode data, particular vector-based algorithms and "dimensionally aware" thresholding mechanisms such as those described further herein should be used. For example, a vector magnitude vs. an n-dimensional "threshold surface" might be applied. For every defect detected, feature vector data can include a difference image magnitude for each of the image channels. This rich dataset can be instrumental in providing sampling and classification algorithms with data that has a basis in physics due to the "spectral response" (different spectral conditions) and/or "geometrical response" (different aperture conditions).

The embodiments described herein can therefore be used to generate different kinds of information for defects or to use different kinds of information to detect the defects in the first place. For example, the systems described herein may be configured to perform spectral imaging in which a complete spectrum or some spectral information is collected at every location in an image plane. In addition, the system embodiments described herein may be configured as imaging spectrometers that can be used to acquire a spectrally-resolved image of a defect or a specimen. The system embodiments described herein may also be configured for hyperspectral imaging in which information is collected and processed from across the electromagnetic spectrum. Such imaging may be performed to find objects, identify materials and the like by obtaining the spectrum for each pixel in an image. Hyperspectral imaging may be different from spectral imaging in that hyperspectral imaging is performed with much finer wavelength resolution compared to spectral imaging and may cover a relatively wide range of wavelengths. The embodiments described herein may also be used for spectroscopy and spectrography in which measurements of radiation intensity as a function of wavelength are performed. The embodiments described herein may also be used to generate color or digital color images of a defect or a specimen. A digital color image may be a digital image that includes color information for every pixel. A color image may be stored as a raster map, a two-dimensional array of small integer triplets, or as three separate raster maps, one for each mode.

Some currently available inspection systems and methods use information from more than one channel or mode to detect defects and/or classify defects. For example, some inspection systems and methods separately detect light scattered from a specimen at different scattering angles and then use information about the light scattered into the different angles to determine whether a defect is one type or another. In addition, some currently used inspection systems and methods may determine defect features based on light detected by different channels or modes and then determine the defect type and/or perform other functions based on those defect features. However, unlike the embodiments described herein, the currently used methods and systems do not store images or other detector output for locations on a specimen unless a defect is detected at the locations. In addition, even for systems and methods that use information from multiple channels or modes to detect or perform other functions for defects, those systems and methods do not store the images or other output of the detectors generated for all of the multiple modes used to inspect a specimen or even one or more modes that did not detect a defect on the specimen. Therefore, unlike the systems and methods described herein, the previously used systems and methods cannot "re-visit" a defect location or any other location with the inspection system by way of images or detector output generated by a mode other than the one(s) that detected a defect unless the specimen is placed back in the inspector for generation of the additional images. Re-positioning the specimen back in the inspector not only takes additional time but any error in reproducibly positioning the specimen in the inspection system can cause the wrong locations on the specimen to be imaged thereby causing error in the information that is generated for a selected defect location.

In an additional embodiment, the one or more computer subsystems are configured for combining the one or more characteristics of the first of the defects with inspection results generated for the specimen by the inspection system thereby generating modified inspection results and sending the modified inspection results to another system configured to perform a process on the physical version of the specimen. For example, data collected as described above for certain defects on a specimen can be merged with data collected through conventional detection methods. The resulting array of values for each location may constitute a full matrix of conventionally collected and unconventionally collected data across the selected mode space. The other system that performs a process on the physical version of the specimen may include, for example, a defect review system, a metrology system, a failure analysis system, etc. In this manner, processes such as defect review, metrology, failure analysis, and the like may be performed based on the modified inspection results, which may include all of the information generated for the defects by the embodiments described herein.

The embodiments described herein may also be configured as described in U.S. Patent Application Ser. No. 62/073, 418 filed on Oct. 31, 2014 by Duffy, which is incorporated by reference as if fully set forth herein. The embodiments described herein may also be configured to perform any steps of any methods described in this patent application.

Each of the embodiments of the system described above may be combined together into one single embodiment. In other words, unless otherwise noted herein, none of the system embodiments are mutually exclusive of any other system embodiments. Furthermore, although FIGS. 2-8 show a variety of functions that may be performed by the computer subsystem(s) described herein, unless otherwise noted herein, none of the functions shown in these figures are essential to the function of the system embodiments described herein and/or practice of the method embodiments described herein. In other words, the embodiments described herein may be configured to perform fewer than all of the functions shown in these figures or more than all of the functions shown in these figures, and the embodiments can still function and/or be practiced within the scope of these embodiments.

Another embodiment relates to a method for determining one or more characteristics for defects detected on a specimen. The method includes storing images for a specimen generated by an inspection system. The inspection system is configured as described herein. The stored images include the images generated for locations on the specimen at which the defects were and were not detected by the inspection system. The method also includes identifying a first of the defects that was detected with a first of the multiple modes but was not detected with one or more other of the multiple modes. In addition, the method includes acquiring, from the stored images, one or more of the images generated with the one or more other of the multiple modes at a location on the specimen corresponding to the first of the defects. The method further includes determining one or more characteristics of the acquired one or more images and determining one or more characteristics of the first of the defects based on the one or more characteristics of the acquired one or more images.

Each of the steps of the method may be performed as described further herein. The method may also include any other step(s) that can be performed by the inspection subsystem and/or computer subsystem(s) described herein. The storing, identifying, acquiring, determining the one or more characteristics of the acquired one or more images, and determining the one or more characteristics of the first of the defects steps are performed by one or more computer subsystems, which may be configured according to any of the embodiments described herein. In addition, the method described above may be performed by any of the system embodiments described herein.

Figure 9:
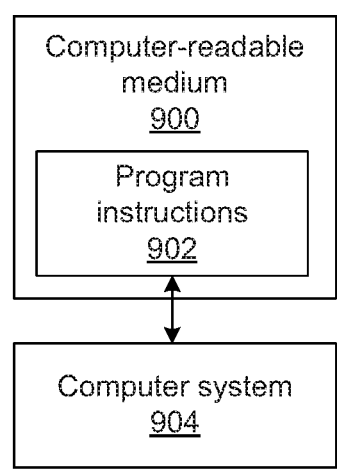
FIG. 9 is a block diagram illustrating one embodiment of a non-transitory computer-readable medium storing program instructions for causing a computer system to perform a computer-implemented method described herein.

An additional embodiment relates to a non-transitory computer-readable medium storing program instructions executable on a computer system for performing a computer-implemented method for determining one or more characteristics for defects detected on a specimen. One such embodiment is shown in FIG. 9. In particular, as shown in FIG. 9, non-transitory computer-readable medium 900 includes program instructions 902 executable on computer system 904. The computer-implemented method may include any step(s) of any method(s) described herein.

Program instructions 902 implementing methods such as those described herein may be stored on computer-readable medium 900. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), SSE (Streaming SIMD Extension) or other technologies or methodologies, as desired.

Computer system 904 may be configured according to any of the embodiments described herein.

Further modifications and alternative embodiments of various aspects of the invention will be apparent to those skilled in the art in view of this description. For example, methods and systems for determining one or more characteristics for defects detected on a specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to detect defects on a specimen, comprising:
   a storage medium configured for storing images for a specimen generated by an inspection system, wherein the inspection system is configured for scanning energy over a physical version of the specimen while detecting energy from the specimen to thereby generate the images for the specimen, and wherein the inspection system is further configured to perform the scanning and the detecting with multiple modes; and
   one or more computer subsystems configured for:
      acquiring, from the storage medium, two or more images generated with two or more of the multiple modes at a location on the specimen; and
      determining if a defect is present at the location based on the acquired two or more images.

2. The system of claim 1, wherein determining if the defect is present comprises determining two or more difference images for the acquired two or more images, respectively, determining two or more difference image attributes for the two or more difference images, respectively, and determining if a defect is present based on a combination of the two or more difference image attributes.

3. The system of claim 1, wherein determining if the defect is present comprises determining two or more image attributes for the acquired two or more images, respectively, and determining if a defect is present based on a combination of the two or more image attributes.

4. The system of claim 1, wherein determining if the defect is present comprises determining two or more image attributes for the acquired two or more images, respectively, and applying a multi-dimensional threshold to a combination of the two or more image attributes.

5. The system of claim 1, wherein the one or more computer subsystems are further configured for determining one or more parameters used for determining if the defect is present based on a portion of a design for the specimen corresponding to the location.

6. The system of claim 1, wherein the one or more computer subsystems are further configured for determining one or more parameters used for determining if the defect is present based on a segment of the acquired two or more images in which the location is located.

7. The system of claim 1, wherein defects are not detected on the specimen by the inspection system.

8. The system of claim 1, wherein the storage medium and the one or more computer subsystems are not part of the inspection system and do not have any capability for handling the physical version of the specimen.

9. The system of claim 1, wherein the storage medium and the one or more computer subsystems are further configured as a virtual inspection system.

10. The system of claim 1, wherein the energy scanned over the specimen comprises light, wherein the energy detected from the specimen comprises light, and wherein at least one of the multiple modes uses at least one wavelength of the light scanned over the specimen that is different from at least one wavelength of the light scanned over the specimen used for at least one other of the multiple modes.

11. The system of claim 1, wherein at least one of the multiple modes uses an illumination channel of the inspection system that is different from an illumination channel of the inspection system used for at least one other of the multiple modes.

12. The system of claim 1, wherein at least one of the multiple modes uses a configuration of an aperture of the inspection system that is different from a configuration of an aperture of the inspection system used for at least one other of the multiple modes.

13. The system of claim 1, wherein at least one of the multiple modes uses a detection channel of the inspection system that is different from a detection channel of the inspection system used for at least one other of the multiple modes.

14. The system of claim 1, wherein the inspection system is further configured to perform the scanning and the detecting with the multiple modes serially in different scans of the specimen performed during a single inspection process for the specimen.

15. The system of claim 1, wherein the inspection system is further configured to perform the scanning and the detecting with at least two of the multiple modes simultaneously in a single scan of the specimen performed during a single inspection process for the specimen.

16. The system of claim 1, wherein the images stored by the storage medium further comprise all of the images generated for the specimen by the inspection system during the scanning and detecting.

17. The system of claim 1, wherein the one or more computer subsystems are further configured for:
identifying a first of defects that was detected on the specimen with a first of the multiple modes but was not detected with one or more other of the multiple modes;
acquiring, from the storage medium, one or more of the images generated with the one or more other of the multiple modes at a location on the specimen corresponding to the first of the defects;
determining one or more characteristics of the acquired one or more images; and
determining one or more characteristics of the first of the defects based on the one or more characteristics of the acquired one or more images.

18. The system of claim 17, wherein at least one of the acquired one or more images comprises a test image, and wherein determining the one or more characteristics of the at least one of the acquired one or more images comprises generating a difference image by subtracting a reference image for the at least one of the acquired one or more images from the test image and determining one or more characteristics of the difference image.

19. The system of claim 17, wherein the first of the defects was detected in two different difference images generated for the location on the specimen corresponding to the first of the defects.

20. The system of claim 17, wherein the first of the defects was detected in only one of multiple difference images generated for the location on the specimen corresponding to the first of the defects.

21. The system of claim 17, wherein the one or more computer subsystems are further configured for binning the first of the defects based on the determined one or more characteristics of the first of the defects.

22. The system of claim 17, wherein the one or more computer subsystems are further configured for classifying the first of the defects based on the determined one or more characteristics of the first of the defects.

23. The system of claim 17, wherein the one or more computer subsystems are further configured for sampling the first of the defects based on the determined one or more characteristics of the first of the defects.

24. The system of claim 17, wherein the one or more computer subsystems are further configured for combining the one or more characteristics of the first of the defects with inspection results generated for the specimen by the inspection system thereby generating modified inspection results and sending the modified inspection results to another system configured to perform a process on the physical version of the specimen.

25. The system of claim 1, wherein the specimen comprises a wafer.

26. The system of claim 1, wherein the specimen comprises a reticle.

27. The system of claim 1, wherein the energy scanned over the specimen comprises light, and wherein the energy detected from the specimen comprises light.

28. The system of claim 1, wherein the energy scanned over the specimen comprises electrons, and wherein the energy detected from the specimen comprises electrons.

29. A non-transitory computer-readable medium, storing program instructions executable on a computer system for performing a computer-implemented method for detecting defects on a specimen, wherein the computer-implemented method comprises:
storing images for a specimen generated by an inspection system, wherein the inspection system is configured for scanning energy over a physical version of the specimen while detecting energy from the specimen to thereby generate the images for the specimen, and wherein the inspection system is further configured to perform the scanning and the detecting with multiple modes;
acquiring, from the stored images, two or more images generated with two or more of the multiple modes at a location on the specimen; and
determining if a defect is present at the location based on the acquired two or more images.

30. A method for detecting defects on a specimen, comprising:
storing images for a specimen generated by an inspection system, wherein the inspection system is configured for scanning energy over a physical version of the specimen while detecting energy from the specimen to thereby generate the images for the specimen, and wherein the inspection system is further configured to perform the scanning and the detecting with multiple modes;

acquiring, from the stored images, two or more images generated with two or more of the multiple modes at a location on the specimen; and determining if a defect is present at the location based on the acquired two or more images.

\* \* \* \* \*